(12) United States Patent
del Rio et al.

(10) Patent No.: US 9,820,756 B2
(45) Date of Patent: *Nov. 21, 2017

(54) CUTTING BURR SHANK CONFIGURATION

(71) Applicant: DePuy Synthes Products, Inc., Raynham, MA (US)

(72) Inventors: Eddy H. del Rio, West Palm Beach, FL (US); Duane Jeffrey Enck, West Palm Beach, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 33 days.

This patent is subject to a terminal disclaimer.

(21) Appl. No.: 15/225,043

(22) Filed: Aug. 1, 2016

(65) Prior Publication Data

US 2016/0338713 A1    Nov. 24, 2016

Related U.S. Application Data

(63) Continuation of application No. 14/223,011, filed on Mar. 24, 2014, now Pat. No. 9,402,638, which is a
(Continued)

(51) Int. Cl.
*A61B 17/16*        (2006.01)

(52) U.S. Cl.
CPC ........ *A61B 17/1617* (2013.01); *A61B 17/162* (2013.01); *A61B 17/1631* (2013.01); *Y10T 408/907* (2015.01)

(58) Field of Classification Search
CPC ... A61B 17/16; A61B 17/1615; A61B 17/162; Y10T 408/907
(Continued)

(56) References Cited

U.S. PATENT DOCUMENTS 170,604 A    11/1875    Williams
170,694 A    12/1875    Williams
(Continued)

FOREIGN PATENT DOCUMENTS

CN    2631675    3/2003
CN    1406700    4/2003
(Continued)

OTHER PUBLICATIONS

Office Action, dated Dec. 16, 2014, received in connection with JP Patent Application No. 2014503639. (English Translation).
(Continued)

*Primary Examiner* — Eric S Gibson
(74) *Attorney, Agent, or Firm* — Meunier Carlin & Curfman LLC

(57) ABSTRACT

A cutting burr that includes a pair of axially spaced diamond-shaped portions designed to be keyed into a spindle of a locking mechanism of a high speed surgical drilling instrument and adapted to fit into a single pawl thereof to lock said cutting burr in place so as to prevent axial movement thereof and provide concentric rotation of said cutting burr without any wobbling. The orientation of both portions may be identical with respect to a center plan and diamond shape in the portion at the proximal end of the shank of the cutting tool may be larger than the intermediately located diamond shape of the other portion. The apexes of the facets of the six-sided diamond shape may be disposed below the surface of the shank of the cutting burr.

13 Claims, 3 Drawing Sheets

Related U.S. Application Data continuation of application No. 13/082,016, filed on Apr. 7, 2011, now Pat. No. 8,690,876.

(58) Field of Classification Search
USPC ....... 606/79–81, 84, 85, 167, 169–171, 180; 81/177.85, 438; 279/35, 37, 77, 78, 89, 279/106, 107, 131, 156; 403/383; 408/226

See application file for complete search history.

(56) References Cited

U.S. PATENT DOCUMENTS

| | | |
|---|---|---|
| RE8,360 E | 8/1878 | Williams |
| 233,707 A | 10/1880 | Starr |
| 233,709 A | 10/1880 | Starr |
| 269,627 A | 12/1882 | Bonner |
| 283,745 A | 8/1883 | Bartlett |
| 287,683 A | 10/1883 | Johnston et al. |
| 302,870 A | 7/1884 | Starr |
| 327,558 A | 10/1885 | Kuder |
| 359,798 A | 3/1887 | Mann |
| 415,983 A | 11/1889 | Star |
| 418,108 A | 12/1889 | Browne |
| 474,011 A | 5/1892 | Harrison |
| 553,226 A | 1/1896 | Brockett |
| 748,398 A | 12/1903 | Middleton |
| 988,154 A | 3/1911 | Thiemer |
| 988,903 A | 4/1911 | Smith |
| 1,135,057 A | 4/1915 | Schultis |
| 1,188,533 A | 6/1916 | Cobey |
| 1,433,590 A | 10/1922 | Ziegler |
| 1,503,962 A | 8/1924 | Milliken |
| 1,578,397 A | 3/1926 | Cone |
| 1,717,663 A | 6/1929 | Checkley |
| 1,726,012 A | 8/1929 | Bilz |
| 1,862,337 A | 6/1932 | Emrick |
| 1,947,957 A | 2/1934 | Tiliman |
| 2,012,280 A | 8/1935 | Johansen |
| 2,101,347 A | 12/1937 | Robinette |
| 2,367,863 A | 1/1945 | Grey |
| 2,390,950 A | 12/1945 | Lanfranconi |
| 2,405,018 A | 7/1946 | Crowley |
| 2,448,817 A | 9/1948 | McArthur |
| 2,473,380 A | 6/1949 | Ljunggren et al. |
| 2,494,166 A | 1/1950 | Drissner |
| 2,543,290 A | 2/1951 | Johansson |
| 2,614,781 A | 10/1952 | Engel |
| 2,686,682 A | 8/1954 | Csaki |
| 2,740,974 A | 4/1956 | Lewis |
| 2,769,643 A | 11/1956 | Denzler |
| 2,787,010 A | 4/1957 | Uphoff |
| 2,874,985 A | 2/1959 | March |
| 2,939,643 A | 6/1960 | Barsam, Jr. |
| 2,955,831 A | 10/1960 | Zandberg et al. |
| 3,046,029 A | 7/1962 | Weber et al. |
| 3,054,308 A | 9/1962 | Larry |
| 3,084,898 A | 4/1963 | Miller |
| 3,136,347 A | 6/1964 | Linguist |
| RE25,804 E | 6/1965 | Misuraca |
| 3,252,667 A | 5/1966 | Miller |
| 3,466,971 A | 9/1969 | Meyer |
| 3,533,638 A | 10/1970 | Sedgwick |
| 3,574,374 A | 4/1971 | Keller et al. |
| 3,589,826 A | 6/1971 | Fenn |
| 3,596,917 A | 8/1971 | Meyer |
| 3,599,996 A | 8/1971 | Holt |
| 4,032,163 A | 6/1977 | Holt |
| 4,055,185 A | 10/1977 | Waldron |
| 4,073,497 A | 2/1978 | Flagg et al. |
| 4,114,276 A | 9/1978 | Malata |
| 4,115,024 A | 9/1978 | Süssmuth |
| 4,131,165 A | 12/1978 | Wanner |
| 4,298,074 A | 11/1981 | Mattchen |
| 4,303,252 A | 12/1981 | Snider |
| 4,325,661 A | 4/1982 | Tickins |
| 4,374,481 A | 2/1983 | Brodie |
| 4,565,472 A | 1/1986 | Brennsteiner et al. |
| 4,632,195 A | 12/1986 | Emmerich |
| 4,710,075 A | 12/1987 | Davison |
| 4,984,667 A | 1/1991 | Tjaden |
| 5,037,251 A | 8/1991 | Roth |
| 5,074,025 A | 12/1991 | Willard, III |
| 5,152,642 A | 10/1992 | Pitts et al. |
| 5,218,890 A | 6/1993 | Christ, Jr. |
| 5,271,697 A | 12/1993 | Johnson et al. |
| 5,421,682 A | 6/1995 | Obermeier et al. |
| 5,433,562 A | 7/1995 | Phillips et al. |
| 5,466,101 A | 11/1995 | Meyen |
| 5,542,846 A | 8/1996 | Quinn et al. |
| 5,601,560 A | 2/1997 | del Rio |
| 5,630,818 A | 5/1997 | del Rio et al. |
| 5,658,305 A | 8/1997 | Baker |
| 5,664,792 A | 9/1997 | Tseng |
| 5,735,535 A | 4/1998 | McCombs et al. |
| 5,741,263 A | 4/1998 | Umber et al. |
| 5,820,136 A | 10/1998 | Han et al. |
| 5,833,246 A | 11/1998 | Trott |
| 5,833,704 A | 11/1998 | McCombs et al. |
| 5,888,200 A | 3/1999 | Walen |
| 5,904,687 A | 5/1999 | del Rio et al. |
| 5,921,563 A | 7/1999 | Huggins et al. |
| 5,941,891 A | 8/1999 | Walen |
| 5,957,634 A | 9/1999 | Carpinetti |
| 6,033,408 A | 3/2000 | Gage et al. |
| 6,045,564 A | 4/2000 | Walen |
| 6,129,363 A | 10/2000 | Mack |
| 6,135,461 A | 10/2000 | Below et al. |
| RE37,358 E | 9/2001 | del Rio et al. |
| 6,302,408 B1 | 10/2001 | Zierpka |
| 6,341,926 B1 | 1/2002 | Liu |
| 6,409,181 B1 | 6/2002 | Hsueh |
| 6,533,235 B1 | 3/2003 | Dymerski et al. |
| 6,533,291 B2 | 3/2003 | Huggins et al. |
| 6,572,311 B2 | 6/2003 | Vasudeva |
| 6,607,533 B2 | 8/2003 | del Rio et al. |
| 6,623,220 B2 | 9/2003 | Nuss et al. |
| 6,705,807 B1 | 3/2004 | Rudolph et al. |
| 6,725,749 B1 | 4/2004 | Liou |
| 6,733,218 B2 | 5/2004 | del Rio et al. |
| 6,769,846 B2 | 8/2004 | Campbell, Jr. et al. |
| 6,780,189 B2 | 8/2004 | Tidwell et al. |
| 7,011,661 B2 | 3/2006 | Riedel et al. |
| 7,028,589 B1 | 4/2006 | Cheng |
| 7,066,940 B2 | 6/2006 | Riedel et al. |
| 7,114,728 B2 | 10/2006 | Chen |
| 7,140,817 B1 | 11/2006 | Phillips et al. |
| 7,207,400 B2 | 4/2007 | Bise et al. |
| 7,258,349 B2 | 8/2007 | Frauhammer et al. |
| 7,316,529 B2 | 1/2008 | Phillips et al. |
| 7,367,762 B2 | 5/2008 | Takase et al. |
| 7,465,309 B2 | 12/2008 | Walen |
| 7,712,746 B2 | 5/2010 | Manschitz et al. |
| 7,845,428 B2 | 12/2010 | Sakamaki et al. |
| 8,273,097 B2 | 9/2012 | Malla et al. |
| 8,403,338 B2 | 3/2013 | Hangleiter |
| 8,690,876 B2 | 4/2014 | del Rio et al. |
| 8,801,713 B2 | 8/2014 | del Rio et al. |
| 9,113,917 B2 | 8/2015 | del Rio et al. |
| 9,381,023 B2 | 7/2016 | Del Rio et al. |
| 9,402,638 B2* | 8/2016 | del Rio ............... A61B 17/162 |
| 2001/0006280 A1 | 7/2001 | Hangleiter |
| 2001/0042964 A1 | 11/2001 | Bedi et al. |
| 2002/0009341 A1 | 1/2002 | Vasudeva |
| 2002/0058958 A1 | 5/2002 | Walen |
| 2002/0151902 A1 | 10/2002 | Riedel et al. |
| 2002/0159850 A1 | 10/2002 | Ravid |
| 2002/0165549 A1 | 11/2002 | Owusu-Akyaw et al. |
| 2003/0060829 A1 | 3/2003 | del Rio et al. |
| 2003/0060841 A1 | 3/2003 | del Rio et al. |
| 2003/0130663 A1 | 7/2003 | Walen |
| 2003/0163134 A1 | 8/2003 | Riedel et al. |
| 2005/0096661 A1 | 5/2005 | Farrow et al. |
| 2006/0049587 A1 | 3/2006 | Cornwell |
| 2006/0053974 A1 | 3/2006 | Blust et al. |

(56) References Cited

U.S. PATENT DOCUMENTS

| | | |
|---|---|---|
| 2008/0119863 A1 | 5/2008 | Mellier |
| 2008/0208195 A1 | 8/2008 | Shores et al. |
| 2008/0208229 A1 | 8/2008 | Tidwell et al. |
| 2009/0146421 A1 | 6/2009 | Engdahl |
| 2009/0273146 A1 | 11/2009 | Dezheng et al. |
| 2009/0326540 A1 | 12/2009 | Estes |
| 2010/0063524 A1 | 3/2010 | McCombs |
| 2010/0219594 A1 | 9/2010 | Nash |
| 2012/0003057 A1 | 1/2012 | Leyba |
| 2012/0259336 A1 | 10/2012 | del Rio et al. |
| 2012/0259337 A1 | 10/2012 | del Rio et al. |
| 2012/0275875 A1 | 11/2012 | Gischus |
| 2013/0130663 A1 | 5/2013 | Jung et al. |
| 2014/0303624 A1 | 10/2014 | del Rio et al. |
| 2015/0032111 A1 | 1/2015 | del Rio et al. |

FOREIGN PATENT DOCUMENTS

| | | |
|---|---|---|
| CN | 1672641 | 9/2005 |
| CN | 2774405 | 4/2006 |
| CN | 2882550 | 3/2007 |
| CN | 101365390 | 2/2009 |
| JP | 02009507 | 1/1990 |
| JP | 03019703 | 1/1991 |
| JP | 07214406 | 8/1995 |
| JP | 2000052114 | 2/2000 |
| JP | 2002137111 | 5/2002 |
| WO | 96/10962 | 4/1996 |
| WO | 2004/082490 | 9/2004 |
| WO | 2008/020828 | 2/2008 |
| WO | 2012/138337 | 10/2012 |
| WO | 2012/138338 | 10/2012 |

OTHER PUBLICATIONS

International Preliminary Report on Patentability and Written Opinion, dated Oct. 8, 2013, received in connection with corresponding International Patent Application No. PCT/US2011/031505.

International Search Report, dated Feb. 28, 2012, received in connection with corresponding International Patent Application No. PCT/US2011/031505.

International Preliminary Report on Patentability and Written Opinion, dated Oct. 8, 2013, received in connection with related International Patent Application No. PCT/US2011/031512.

International Search Report, dated Jan. 4, 2012, received in connection with related International Patent Application No. PCT/US2011/031512.

Co-pending U.S. Appl. No. 15/171,232, filed Jun. 2, 2016.

* cited by examiner

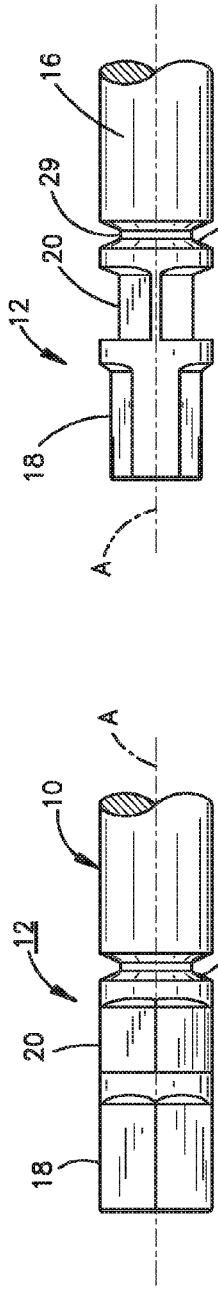
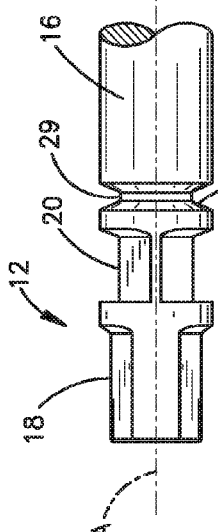
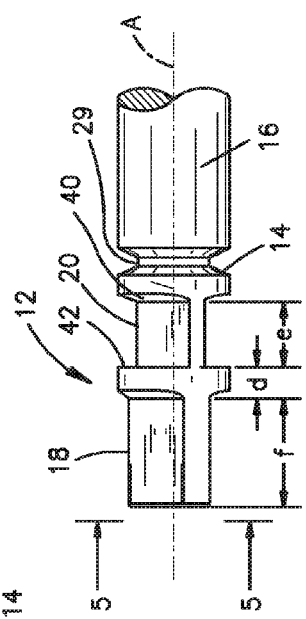
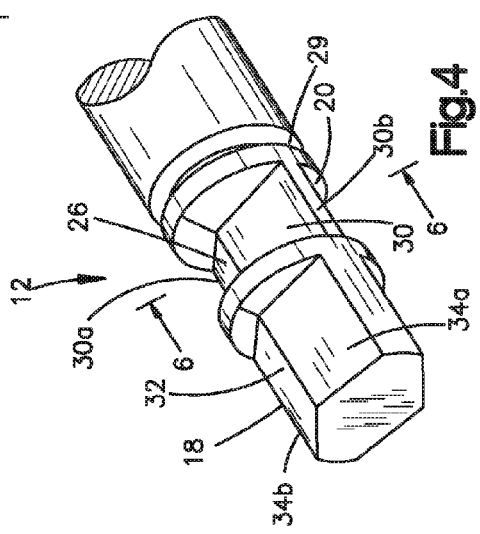
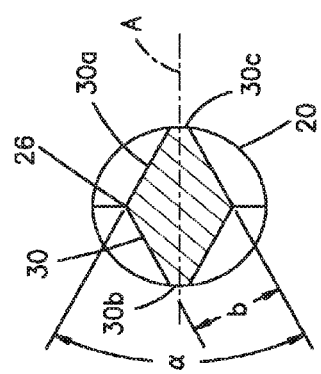

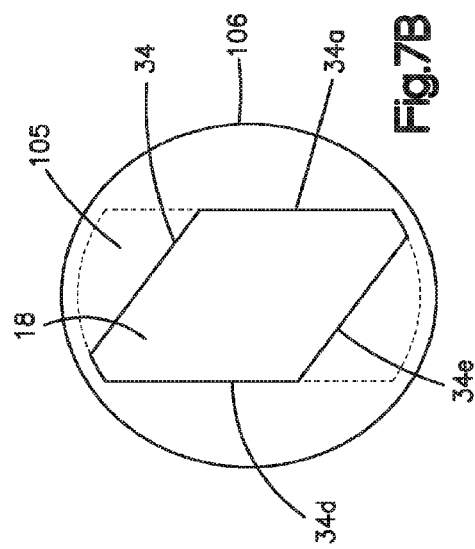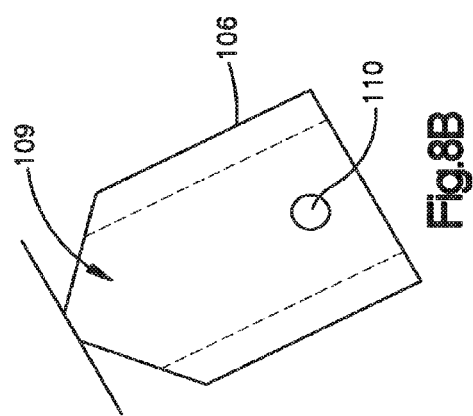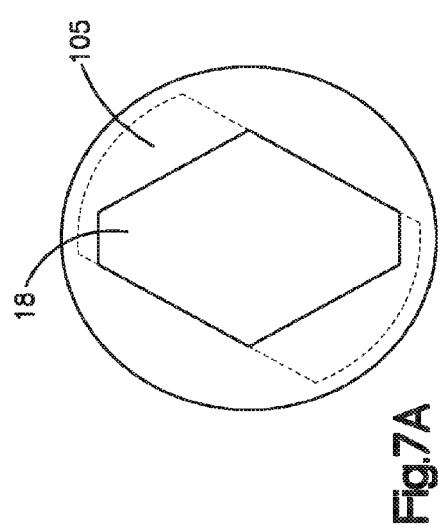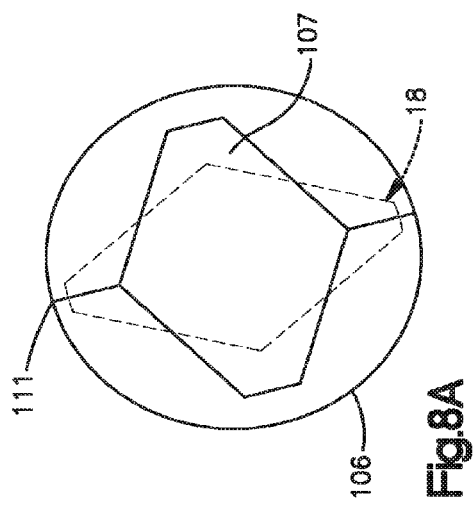

CUTTING BURR SHANK CONFIGURATION

CROSS-REFERENCE TO RELATED APPLICATIONS

The subject matter described in this application is related to subject matter disclosed in the following commonly assigned applications: U.S. patent application Ser. No. 14/223,011 (now U.S. Pat. No. 9,402,638), filed Mar. 24, 2014, entitled "CUTTING BURR SHANK CONFIGURATION," and U.S. patent application Ser. No. 13/082,016 (now U.S. Pat. No. 8,690,876), filed on Apr. 7, 2011, entitled "CUTTING BURR SHANK CONFIGURATION," which are incorporated herein by reference in their entirety.

BACKGROUND

When performing surgery, surgeons may utilize a surgical drilling instrument for drilling, cutting or shaping bones that utilize a numerous different kinds and sizes of cutting burrs and attachments. During certain medical operations, the cutting burr needs to be changed. The change must be done timely and efficiently in view of the surgical demands. To this end, the portion of the cutting burr, namely, the proximate end of the shank typically lacks a configuration to accommodate this change of the cutting burr.

SUMMARY

Disclosed herein is a cutting burr that provides for a quick release that is fast and simple, and which facilitates the insertion of the cutting burr into a surgical drilling instrument. The cutting burr may have a pair of axially spaced six sided diamond-shaped portions, where one diamond-shaped portion may be formed at an edge of the proximal end of the cutting burr and provides a positive connection with a drive spindle that is connected to a drive motor of the surgical drilling instrument. A second, axially disposed diamond-shaped portion is adapted to mate with a locking pawl of the surgical drilling instrument. The locking pawl engages the axially disposed diamond-shaped portion to lock the cutting burr into the surgical drilling instrument with substantially no axial movement.

In some implementations, a detent pawl is provided to hold the cutting burr within the surgical instrument when it is in a loading position. The detent pawl may engage the axially disposed diamond-shaped portion at a side opposite the locking pawl.

In some implementations, the diamond-shaped portion at the proximal end is sized such that it can be used with older surgical drilling instruments that may not be provided with a complementary receiving recess for the diamond-shaped portion.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary is better understood when read in conjunction with the appended drawings. For the purposes of illustration, there is shown in the drawings exemplary implementations; however, these implementations are not limited to the specific methods and instrumentalities disclosed. In the drawings:

FIG. 1 a fragmentary top plan view illustrating the axially spaced six-sided diamond-shaped cut out portion or portions formed on the proximate end of the shank of the cutting burr;

FIG. 2 is a perspective view of FIG. 1;

FIG. 3 is another prospective view of FIG. 1 slightly turned illustrating one of the facets in each of the six-sided diamond-shaped portions;

FIG. 4 is another perspective view of FIG. 2 slightly turned illustrating the top facets of the six-sided diamond-shaped portions;

FIG. 5 is an end view taken along lines 5-5 of FIG. 3 illustrating the shape of the six-sided diamond-shaped portion formed in the cutting burr shank;

FIG. 6 is a sectional view taken along lines 6-6 of FIG. 4 illustrating the shape of the six-sided diamond-shaped portion and illustrating the different sizes and the orientation of the six-sided diamond portion formed in the cutting burr shank;

FIGS. 7A and 7B illustrate a backwards compatibility of the cutting burr of FIGS. 1-6 within a receiving portion of conventional surgical drill;

FIGS. 8A and 8B illustrate a self-alignment aspect of the diamond-shaped portion at a proximal end of the cutting burr in relation to a keyed slot of a surgical drill;

DETAILED DESCRIPTION

Figure 9:
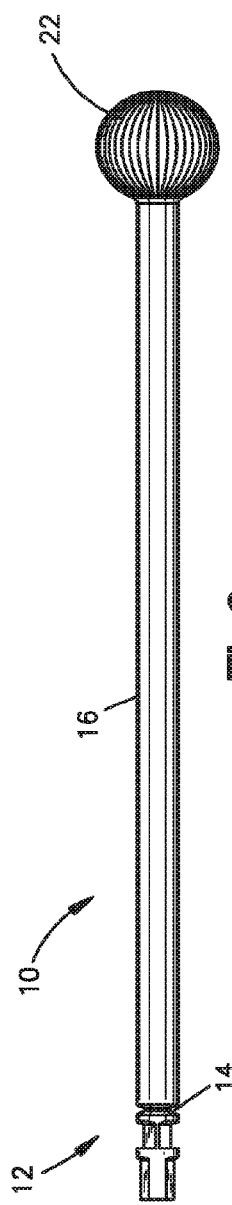
FIG. 9 is an elevated view of the cutting burr with a spherical shaped cutting bit illustrating the diamond-shaped portions formed in the shank thereof.

As used herein, the term "cutting burr" may be analogous with terms such as bit, drill bit, surgical drill bit and the like. The term "attachment" may have several meanings within the text of this application, but when generalized as a component of a surgical drilling instrument it refers to a portion of the instrument that attaches to the end of the motor/locking mechanism and receives the cutting burr. An "attachment" may be a controlled depth attachment, a minimally invasive attachment and the like. The surgical drilling instrument may include an integral motor (electric or pneumatic) and a locking mechanism and an attachment releasably connected to the locking mechanism.

High speed surgical drills are increasingly being used by surgeons when performing delicate bone dissection in areas such as the cervical and lumbar spine. Such surgical drills operate at very high R.P.M., and are able to rotationally drive multiple types of attachments and cutting burrs. As will be described below, a cutting burr of the present disclosure includes a shank that defines two substantially diamond-shaped portions. The substantially diamond-shaped portions provide for ease of insertion and removal of the cutting burr to and from a compatible surgical drill. The substantially diamond-shaped portions also enable the surgical drill to direct higher levels of torque to the cutting burr during surgical procedures.

Referring to FIGS. 1-6, the cutting burr is generally illustrated by reference numeral 10. The attachment portion 12 of the shank 16 of the cutting burr 10 is generally shown as reference numeral 12. A proximal end 14 of the shank 16 is formed with a pair of axially spaced six-sided diamond-shaped portions 18 and 20. As shown in FIGS. 4 and 5, an upper surface of portion 18 includes an apex 32 and a pair of facets 34 and 34a also fairing to side edges 34b and 34c. The side edges 34b and 34c may be curved to match the radius of curvature of an outer surface of the shank 16. As shown in FIGS. 4 and 6, an upper surface 24 of the portion 20 includes apex 26 and a pair of facets 30 and 30a fairing from the apex 26 to the side edges 30b and 30c. The side edges 30b and 30c may be curved to match the radius of curvature of an outer surface of the shank 16.

As shown in the Figs. the diametrical dimensions of the vertices in both portions is less than the diameter of the main body of the shank. The shank 16 may include an annular groove 29. The lower surfaces of the pair of six-sided diamond portions 18 and 20 are a mirror image of the upper surface. While the diamond-shaped portions 18 and 20 are described as being "diamond-shaped," it is noted that such terminology is intended to encompass any six-sided (hexagon) shape having a cross-section with flat edges that meet at a six vertices, curved edges that meet at six points, or some combination of both to form the six sides. The flat and curved edges, and combinations thereof, may be applied to other polygon shapes having different numbers of sides.

The diamond-shaped portion 18 at the outermost proximal end is designed to be inserted into a mating drive portion of a surgical drill, as will be described with reference to FIGS. 8A and 8B. The diamond-shaped portion 20 is provided as an abutment surface of a retractable locking pawl of the surgical drill to provide axial locking of the shank 16 within the surgical drill. The locking pawl may axially abut the adjacent abutment surface of the diamond-shaped portion 20 to axially lock the cutting burr 10 in place, thus providing substantially zero axial movement. For example, an engagement portion of locking pawl may be contoured having a generally V-shape with inner surfaces that fit against the facets 30 and 30a of the diamond-shaped portion 20.

As shown in FIG. 3, a back wall 42 may be formed perpendicular with relation to the central line A and faces a front wall 40 that is tapered from the facet (e.g., 30a) to the outside diameter of the shank 16. In accordance with some aspects, an engagement face of the locking pawl may abut against the back wall 42 to provide axial locking of the cutting burr 10 within the surgical drill. A tapered front wall 40 may facilitate the engagement of the locking pawl into the diamond-shaped portion 20.

The diamond-shaped portion 20 may also be engaged by a detent pawl of the surgical drill. For example, an engagement end of detent pawl may be contoured, e.g., having a generally hill shape to partially fit into the diamond-shaped portion 20 on an opposite side of the engagement end of the locking pawl. The detent pawl may be provided to apply a sufficient force on the diamond-shaped portion 20 to allow the cutting burr 10 to be moved in and out of the surgical drill, while reducing the likelihood that the cutting burr will inadvertently fall out of the surgical drill when in a loading position.

As shown by the a comparison of the sectional views of the diamond-shaped portions 18 and 20 (FIGS. 5 and 6), the two diamond shapes may be different in size, where the diamond shape in diamond-shaped portion 18 is larger than the diamond shape of the diamond-shaped portion 20. As illustrated, the vertices 32 and 36 fall below the outer diameter of the shank 16 and both diamond shapes are in axial alignment with each other and may be oriented in parallel relationship. In some implementations, the diamond-shaped portion 20 and the diamond-shaped portion 18 may be the same size, or the diamond-shaped portion 18 may be larger than the diamond-shaped portion 20. In the various configurations, the vertices 26 and 32 of diamond-shaped portions 20 and 18, respectively, are along a same line and in a same plane as the center line A. Exemplary dimensions of the six-sided diamond diamond-shaped portions 18 and 20 are listed in degrees (°) and inches (") and may be substantially as follows:

The angle of the facets of the six-sided diamond in the diamond-shaped portion 20—a=47°;

The width of the facets of the six-sided diamond in the diamond-shaped portion 20—b=0.046";

The width of the facets of the six-sided diamond in the diamond-shaped portion 18—c=0.065";

The width of the shank 16 at the space between diamond-shaped portions 18 and 20—d=0.029";

The length of the diamond-shaped portion 20—e=0.068"; and

The length between the proximal end and the back wall of diamond-shaped portion 18 f=0.149". This dimension may contribute to the feature of substantially reducing the axial play of the cutting burr.

Thus, in accordance with the above, the diamond-shaped portions 18 and 20 provide sufficient cross-sectional dimensions to meet strength and reliability requirements needed for high-speed, large force surgical applications. Facets 34 and 34a of the diamond shape 18 provide positive engagement surfaces in both clockwise and counter-clockwise rotational directions and are sufficiently sized to withstand rotations forces in either direction without wobbling within the surgical drill. For example, some surgical drills provide bi-directional rotation, allowing the surgeon to selectively reverse rotation for various surgical techniques. In conventional designs, there may be rotational play between a bit end and a drive portion. However, the symmetrical diamond facets 34 and 34a of the diamond-shaped portion 18 provide substantial drive surfaces in either direction.

With reference to FIGS. 7A and 7B, the diamond-shaped portion 18 at the outermost proximal end of the cutting burr 10 is designed to have unidirectional backward compatibility with older drill instruments in accordance with aspects of the disclosure. For example, a conventional drill instrument may include an insert 106 that defines a generally rectangular slot 105 having rounded side walls. The rounded side walls may be shaped with a radius of curvature that parallels the outer wall of the insert 106. Conventional cutting burrs may include a complementary generally rectangular portion having rounded side walls that is received by the slot 105. The insert 106 may be driven by a motor, thus providing rotational force on the cutting burr.

As shown in FIG. 7A, in accordance with some implementations, facets 34a and 34d of the diamond-shaped portion 18 engage the inner walls of the slot 105. The dimension c of the diamond-shaped portion 18, noted above, may be sized such that the surface area of the facets 34a and 34d is substantial enough to withstand the torque provided by the motor of the conventional drill instrument. Thus, the cutting burr 10 of the present disclosure may be utilized by conventional drill instruments.

Referring now to FIGS. 8A and 8B, in some implementations, the cutting burr 10 of the present disclosure provides for a level of self-alignment within the insert 106. The insert 106 may be provided in a compatible surgical drill and define a diamond-shaped key slot 107, a pointed shaped inlet end 109, and opposing holes 110 that formed in the insert 106 for receiving dowel pin which may serve to locate the cutting burr 10 when inserted into the key slot 107. The inlet end 109 serves to facilitate the alignment and insertion of the cutting burr 10 as it is advanced toward and into the key slot 107 of the insert 106. For example, if the diamond-shaped portion 18 is not in alignment with the key slot 107 (FIG. 8A), a bottom surface of the diamond-shaped portion 18 will contact an apex 111 of the inlet end 109 causing the cutting burr 10 to rotate into alignment with the key slot 107. As such, the cooperative engagement of the diamond-shaped portion 18 and inlet end 109 facilitates the easy insertion of the cutting burr 10 into the compatible surgical drill. As such, the diamond portion 18 serves to provide a secure connection in the key slot 107.

Figure 10:
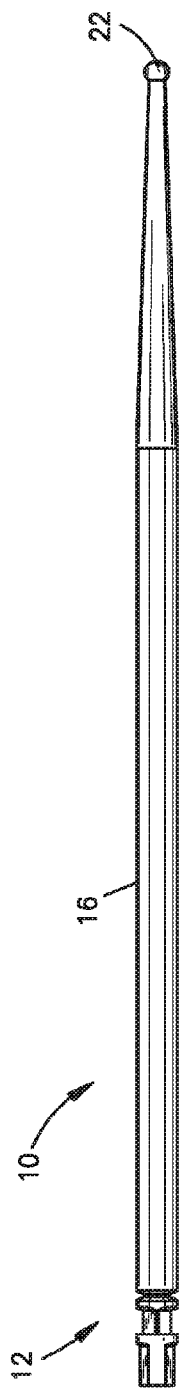
FIG. 10 is another elevated view of an example cutting burr.
Figure 11:
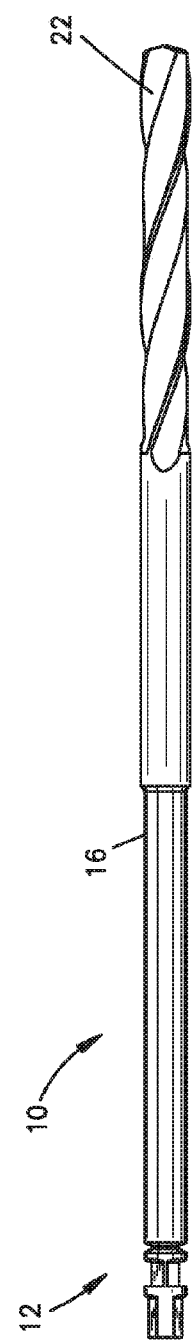
FIG. 11 is another elevated view of an example cutting burr.

FIGS. 9, 10, and 11 illustrate different example cutting bits 22 provided at a distal end on the shank 16. As described above, the shank 16 may include the attachment portion 12. The cutting bits 22 may be milled or cut-out portions. The cutting burr 10 in FIG. 9 exemplifies a fluted ball or drill bit; the cutting burr 10 in FIG. 10 exemplifies a diamond ball; and the cutting burr 10 in FIG. 11 exemplifies a twist drill. The cutting bits 22 are presented only as examples and are not intended to limit the scope of the present disclosure as numerous variations are possible.

Thus, as described above, a cutting burr is provided with an attachment end that has a configuration and dimensions that serve to facilitate the insertion of the cutting burr into the surgical cutting instrument. When locked in the running position there is a structure that prevents the cutting burr from having any axial movement. Also, there is a positive connection such that the cutting burr rotates concentrically without any wobbling motion.

While particular aspects of the present subject matter described herein have been shown and described, it will be apparent to those skilled in the art that, based on the teachings herein, changes and modifications may be made without departing from the subject matter described herein and its broader aspects and, therefore, the appended claims are to encompass within their scope all such changes and modifications as are within the true spirit and scope of the subject matter described herein.

What is claimed:

1. A cutting burr having a shank and an engagement end formed at a proximal end of the shank, comprising:
   a pair of axially spaced six-sided diamond-shaped members formed at the proximal end of the shank, each of the pair of six-sided diamond-shaped members being oriented in a same direction and in parallel planes, wherein each of the pair of six-sided diamond-shaped members comprise a flanged portion with tapered surfaces,
   wherein a back wall of the flanged portion of a first six-sided diamond-shaped member is perpendicular to a center line of the shank and faces a front wall of the flanged portion of a second six-sided diamond-shaped portion,
   wherein apexes of each of the six-sided diamond-shaped members are in axial alignment,
   wherein the one of the pair of six-sided diamond-shaped members is adapted to be inserted into a surgical drill and to accept rotational engagement forces, and
   wherein the other of the pair of six-sided diamond-shaped members is adapted to be engaged by a locking pawl to prevent axial movement of the cutting burr.

2. The cutting burr of claim 1, wherein the apexes of the six-sided members are formed between facets thereof.

3. The cutting burr of claim 1, wherein facets of the six-sided members are formed in parallel planes and are substantially flat.

4. The cutting burr of claim 1, wherein facets of one of the pair of six-sided diamond-shaped members are formed at a predetermined angle to be adapted to receive the locking pawl having a complementary shape.

5. The cutting burr of claim 1, wherein facets of one of the pair of six-sided diamond-shaped members are adapted to receive a generally hill-shaped detent pawl that partially fits into the one of the pair of six-sided diamond-shaped members on an opposite side of the locking pawl.

6. The cutting burr of claim 1, wherein the six-sided diamond-shaped members are different sizes.

7. The cutting burr of claim 1, wherein the apexes are disposed below a surface of the shank.

8. The cutting burr of claim 1, wherein the pair of six-sided members are each formed having side edges that are arched having a radius of curvature of an outside diameter of the shank.

9. A cutting burr, comprising:
   a cylindrically shaped shank;
   a cutting bit formed at a distal end of the cutting burr; and
   an attachment portion formed at a proximal end of the cutting burr, the attachment portion defining a first diamond-shaped portion at a proximal end of the attachment portion, and a second diamond-shaped portion at an axially spaced intermediate position that is a predetermined distance from the first diamond-shaped portion,
   wherein the first diamond-shaped portion and the second diamond-shaped portion have axially aligned apexes and respective facets disposed within parallel planes,
   wherein both the first diamond shaped portion and the second diamond shaped portion comprise a flanged portion with tapered surfaces,
   wherein a back wall of the flanged portion of the first diamond-shaped portion is perpendicular to a center line of the cutting burr and faces a front wall of the flanged portion of the second diamond-shaped portion,
   wherein the first diamond-shaped portion is adapted to receive clockwise or counterclockwise rotation forces applied by a surgical drill having a complementary keyed slot to receive the first diamond-shaped portion, and
   wherein the second diamond-shaped portion is adapted to be axially locked within the surgical drill.

10. The cutting burr of claim 9, wherein the second diamond-shaped portion is adapted to be engaged by a locking pawl to axially lock the cutting burr within the surgical drill.

11. The cutting burr of claim 10, wherein a back wall of the second diamond-shaped portion is adapted to be engaged by an engagement end of the locking pawl.

12. The cutting burr of claim 9, wherein the second diamond-shaped portion is adapted to be engaged by a detent pawl of the surgical drill to hold the cutting burr in place when the surgical drill is in a loading position.

13. The cutting burr of claim 9, wherein a width of facets of the first diamond-shaped portion are sized to provide unidirectional backward compatibility with other surgical drills having different shaped slots than the complementary keyed slot.

\* \* \* \* \*